(12) United States Patent
Blumenkranz et al.

(10) Patent No.: US 10,722,108 B2
(45) Date of Patent: Jul. 28, 2020

(54) SYSTEMS AND METHODS FOR CLEANING AN ENDOSCOPIC INSTRUMENT

(71) Applicant: Intuitive Surgical Operations, Inc., Sunnyvale, CA (US)

(72) Inventors: Stephen J. Blumenkranz, Los Altos, CA (US); Federico Barbagli, San Francisco, CA (US); Tao Zhao, Sunnyvale, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 453 days.

(21) Appl. No.: 15/503,589

(22) PCT Filed: Aug. 11, 2015

(86) PCT No.: PCT/US2015/044633
§ 371 (c)(1),
(2) Date: Feb. 13, 2017

(87) PCT Pub. No.: WO2016/025465
PCT Pub. Date: Feb. 18, 2016

(65) Prior Publication Data
US 2017/0238795 A1    Aug. 24, 2017

Related U.S. Application Data

(60) Provisional application No. 62/037,299, filed on Aug. 14, 2014.

(51) Int. Cl.
*A61B 1/12*    (2006.01)
*A61B 1/00*    (2006.01)
(Continued)

(52) U.S. Cl.
CPC .......... *A61B 1/126* (2013.01); *A61B 1/00091* (2013.01); *B08B 3/02* (2013.01); *B08B 5/02* (2013.01)

(58) Field of Classification Search
None
See application file for complete search history.

(56) References Cited

U.S. PATENT DOCUMENTS

| | | |
|---|---|---|
| 4,281,646 A | 8/1981 | Kinoshita |
| 4,509,507 A | 4/1985 | Yabe |

(Continued)

FOREIGN PATENT DOCUMENTS

| | | |
|---|---|---|
| EP | 0051862 A1 | 5/1982 |
| JP | S5784030 A | 5/1982 |

(Continued)

OTHER PUBLICATIONS

Extended European Search Report for Application No. EP15831277.7, dated Mar. 22, 2018, 8 pages.

(Continued)

*Primary Examiner* — Cristi J Tate-Sims
(74) *Attorney, Agent, or Firm* — Haynes and Boone, LLP

(57) ABSTRACT

A system comprises a nozzle and a pressure augmenting mechanism connected to the nozzle. The pressure augmenting mechanism is configured to provide a pressurized fluid at a pressure that is higher than a standard operating room pressure. The system further comprises a valve between the pressure augmenting mechanism and the nozzle, the valve configured to control provision of the pressurized fluid from the pressure augmenting mechanism. The system further comprises a valve control mechanism and a control system configured to instruct the valve control mechanism to open the valve to release a flow of the pressurized fluid from the pressure augmenting mechanism through the nozzle and (Continued)

over a surface of a medical instrument. An amount of the flow of the pressurized fluid is determined based on a position of the medical instrument in a patient anatomy.

20 Claims, 8 Drawing Sheets

(51) Int. Cl.
*B08B 3/02* (2006.01)
*B08B 5/02* (2006.01)

(56) References Cited

U.S. PATENT DOCUMENTS

| | | | |
|---|---|---|---|
| 4,919,113 | A | 4/1990 | Sakamoto et al. |
| 5,191,878 | A | 3/1993 | Iida et al. |
| 5,437,626 | A * | 8/1995 | Cohen ................ A61B 1/00165 600/109 |
| 5,647,840 | A | 7/1997 | Damelio et al. |
| 5,882,589 | A | 3/1999 | Mariotti |
| 6,309,347 | B1 * | 10/2001 | Takahashi ............... A61B 1/015 600/159 |
| 7,316,681 | B2 | 1/2008 | Madhani et al. |
| 9,259,274 | B2 | 2/2016 | Prisco |
| 9,452,276 | B2 | 9/2016 | Duindam et al. |
| 2002/0001537 | A1 | 1/2002 | Hlebovy et al. |
| 2003/0190256 | A1 * | 10/2003 | Halstead ................ A61B 1/123 422/28 |
| 2007/0255107 | A1 * | 11/2007 | Kawanishi ......... A61B 1/00068 600/159 |
| 2008/0188715 | A1 | 8/2008 | Fujimoto |
| 2009/0247831 | A1 | 10/2009 | Miyamoto et al. |
| 2011/0273549 | A1 * | 11/2011 | Kase .................. A61B 1/00147 348/68 |
| 2012/0059222 | A1 * | 3/2012 | Yoshida ............. A61B 1/00091 600/157 |
| 2013/0217970 | A1 * | 8/2013 | Weisenburgh, II .... A61B 1/015 600/157 |
| 2013/0267891 | A1 | 10/2013 | Malhi et al. |

FOREIGN PATENT DOCUMENTS

| | | |
|---|---|---|
| JP | S57164032 A | 10/1982 |
| JP | H11253393 A | 9/1999 |
| JP | 2007296164 A | 11/2007 |
| JP | 2012045325 A | 3/2012 |
| JP | 2013154171 A | 8/2013 |

OTHER PUBLICATIONS

Co-pending U.S. Appl. No. 62/048,204, filed Sep. 10, 2014.
International Preliminary Report on Patentability for Application No. PCT/US2015/044633, dated Feb. 23, 2017, 14 pages.
International Search Report and Written Opinion for Application No. PCT/US15/44633, dated Nov. 19, 2015, 17 pages.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.
Office Action dated Jun. 25, 2019 for Japanese Application No. 20170507966 filed Aug. 11, 2015, 10 pages.

\* cited by examiner

SYSTEMS AND METHODS FOR CLEANING AN ENDOSCOPIC INSTRUMENT

RELATED APPLICATIONS

This patent application is the U.S. National Phase of International Application No. PCT/US2015/044633, filed Aug. 11, 2015, which designated the U.S. and claims priority to and the benefit of U.S. Provisional Patent Application No. 62/037,299, filed Aug. 14, 2014 and entitled "SYSTEMS AND METHODS FOR CLEANING AN ENDOSCOPIC INSTRUMENT," all of which are incorporated by reference herein in their entireties.

FIELD

The present disclosure is directed to systems and methods for cleaning, and more particularly, to systems and methods for cleaning an endoscopic instrument while inside of a patient.

BACKGROUND

Minimally invasive medical techniques are intended to reduce the amount of tissue that is damaged during medical procedures, thereby reducing patient recovery time, discomfort, and harmful side effects. Such minimally invasive techniques may be performed through natural orifices in a patient anatomy or through one or more surgical incisions. Clinicians may insert medical tools through these natural orifices or incisions to reach a target tissue location. Medical tools include instruments such as therapeutic instruments, diagnostic instruments, and surgical instruments. To reach the target tissue location, a minimally invasive medical tool may navigate natural or surgically created passageways in anatomical systems such as the lungs, the colon, the intestines, the kidneys, the heart, the circulatory system, or the like.

Minimally invasive medical procedures may rely upon visualization systems to find a target location and perform various operations. Particularly, a visualization system may help a minimally invasive medical instrument navigate natural or surgically created passageways in anatomical systems to reach the target tissue location. For example, the visualization system may help guide the minimally invasive medical instrument through natural passageways in the lungs, the colon, the intestines, the kidneys, the heart, the circulatory system, or the like. Some minimally invasive medical instruments may be teleoperated or otherwise computer-assisted.

During navigation of the medical instrument, or during an operation performed by the medical instrument, the lens of the visualization system may become obstructed or clouded by patient tissue or fluids. Such obstructions can make navigation or operation more difficult. Thus, it is desirable to clean the lens of the visualization system in a manner that is safe for the patient.

SUMMARY

The embodiments of the invention are summarized by the claims that follow below.

In one embodiment, a method includes providing a medical instrument, initiating a flow of a pressurized fluid across a surface of the medical instrument, the pressurized fluid having a pressure that is greater than a standard operating room supply, and terminating the flow of the pressurized fluid after a predetermined duration.

In another embodiment, a method includes providing a pressurized fluid with a pressure augmenting mechanism and passing a flow of the pressurized fluid across a surface of a medical instrument. The pulse of pressurized fluid extends for a predetermined duration.

In another embodiment, a system includes a medical instrument, a nozzle, a pressure augmenting mechanism connected to the nozzle, a valve between the pressure augmenting mechanism and the nozzle, and a valve control mechanism configured to control the valve to release a flow of pressurized fluid, for a predetermined duration, from the pressurized augmenting mechanism through the nozzle and over a surface of the medical instrument.

BRIEF DESCRIPTIONS OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In addition, the present disclosure may repeat reference numerals and/or letters in the various examples. This repetition is for the purpose of simplicity and clarity and does not in itself dictate a relationship between the various embodiments and/or configurations discussed.

DETAILED DESCRIPTION

Figure 1:
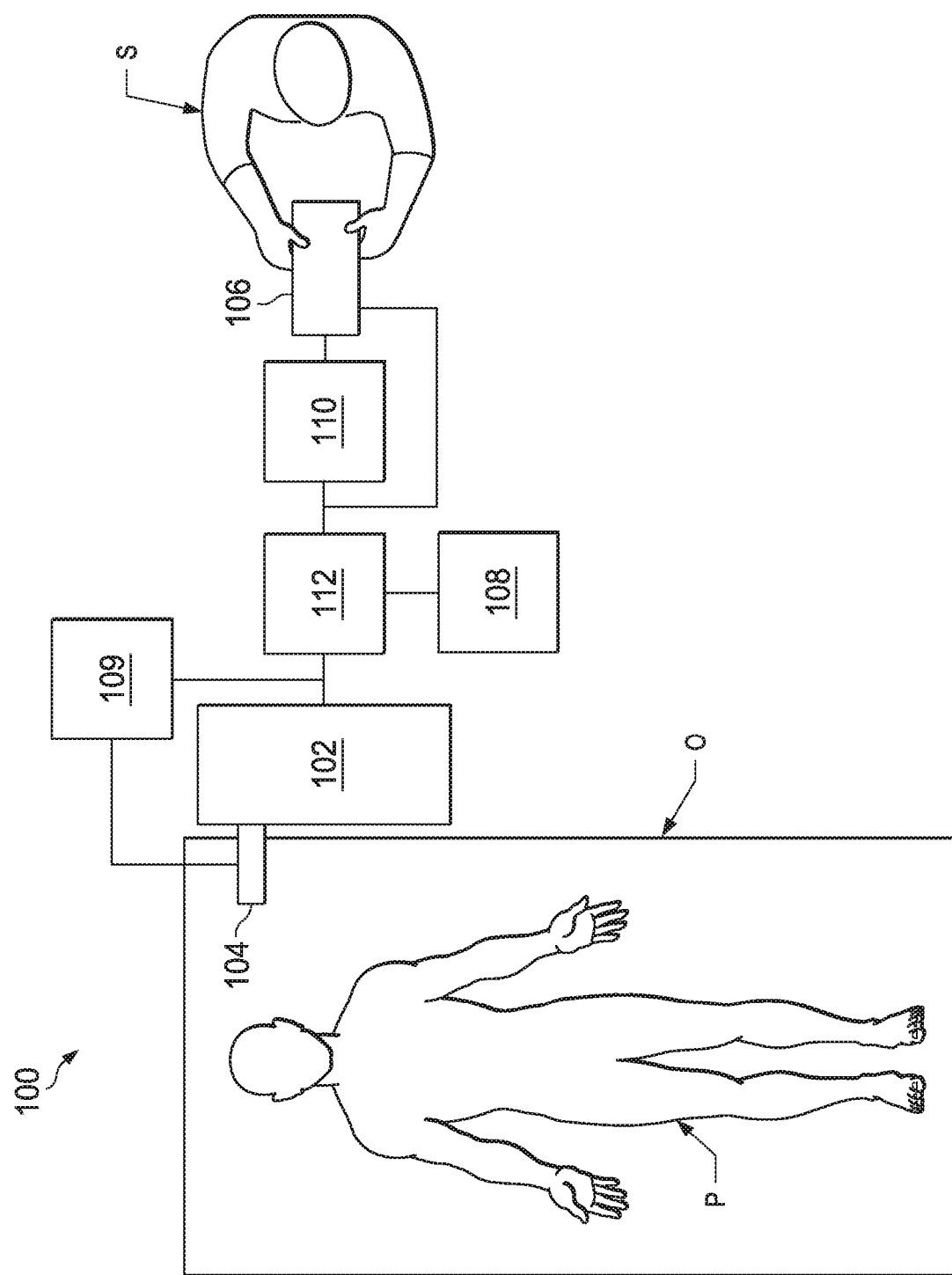
FIG. 1 is a diagram showing an illustrative teleoperational medical system, according to one example of principles described herein.

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. In the following detailed description of the aspects of the invention, numerous specific details are set forth in order to provide a thorough understanding of the disclosed embodiments. However, it will be obvious to one skilled in the art that the embodiments of this disclosure may be practiced without these specific details. In other instances well known methods, procedures, components, and circuits have not been described in detail so as not to unnecessarily obscure aspects of the embodiments of the invention.

Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. In addition, dimensions provided herein are for specific examples and it is contemplated that different sizes, dimensions, and/or ratios may be utilized to implement the concepts of the present disclosure. To avoid needless descriptive repetition, one or more components or actions described in accordance with one illustrative embodiment can be used or omitted as applicable from other illustrative embodiments. For the sake of brevity, the numerous iterations of these combinations will not be described separately. For simplicity, in some instances the same reference numbers are used throughout the drawings to refer to the same or like parts.

The embodiments below will describe various instruments and portions of instruments in terms of their state in three-dimensional space. As used herein, the term "position" refers to the location of an object or a portion of an object in a three-dimensional space (e.g., three degrees of translational freedom along Cartesian X, Y, Z coordinates). As used herein, the term "orientation" refers to the rotational placement of an object or a portion of an object (three degrees of rotational freedom—e.g., roll, pitch, and yaw). As used herein, the term "pose" refers to the position of an object or a portion of an object in at least one degree of translational freedom and to the orientation of that object or portion of the object in at least one degree of rotational freedom (up to six total degrees of freedom). As used herein, the term "shape" refers to a set of poses, positions, or orientations measured along an object.

According to various embodiments, medical procedures, such as biopsy procedures, may be performed using a teleoperational system to guide instrument delivery. Referring to FIG. 1 of the drawings, a teleoperational medical system for use in, for example, medical procedures including diagnostic, therapeutic, or surgical procedures, is generally indicated by the reference numeral 100. As will be described, the teleoperational medical systems of this disclosure are under the teleoperational control of a surgeon. In alternative embodiments, a teleoperational medical system may be under the partial control of a computer programmed to perform the procedure or sub-procedure. In still other alternative embodiments, a fully automated medical system, under the full control of a computer programmed to perform the procedure or sub-procedure, may be used to perform procedures or sub-procedures. As shown in FIG. 1, the teleoperational medical system 100 generally includes a teleoperational assembly 102 mounted to or near an operating table O on which a patient P is positioned. A medical instrument system 104 is operably coupled to the teleoperational assembly 102. An operator input system 106 allows a surgeon or other type of clinician S to view images of or representing the surgical site and to control the operation of the medical instrument system 104. The operator input system 106 may be referred to as a master or surgeon's console.

The operator input system 106 may be located at a surgeon's console, which is usually located in the same room as operating table O. It should be understood, however, that the surgeon S can be located in a different room or a completely different building from the patient P. Operator input system 106 generally includes one or more control device(s) for controlling the medical instrument system 104. More specifically, in response to the surgeon's input commands, the control system 112 effects servomechanical movement of medical instrument system 104. The control device(s) may include one or more of any number of a variety of input devices, such as hand grips, joysticks, trackballs, data gloves, trigger-guns, hand-operated controllers, voice recognition devices, touch screens, body motion or presence sensors, and the like. In some embodiments, the control device(s) will be provided with the same degrees of freedom as the medical instruments of the teleoperational assembly to provide the surgeon with telepresence, the perception that the control device(s) are integral with the instruments so that the surgeon has a strong sense of directly controlling instruments as if present at the surgical site. In other embodiments, the control device(s) may have more or fewer degrees of freedom than the associated medical instruments and still provide the surgeon with telepresence. In some embodiments, the control device(s) are manual input devices which move with six degrees of freedom, and which may also include an actuatable handle for actuating instruments (for example, for closing grasping jaws, applying an electrical potential to an electrode, delivering a medicinal treatment, and the like).

The teleoperational assembly 102 supports the medical instrument system 104 and may include a kinematic structure of one or more non-servo controlled links (e.g., one or more links that may be manually positioned and locked in place, generally referred to as a set-up structure) and a teleoperational manipulator. The teleoperational assembly 102 includes plurality of motors that drive inputs on the medical instrument system 104. These motors move in response to commands from the control system (e.g., control system 112). The motors include drive systems which when coupled to the medical instrument system 104 may advance the medical instrument into a naturally or surgically created anatomical orifice. Other motorized drive systems may move the distal end of the medical instrument in multiple degrees of freedom, which may include three degrees of linear motion (e.g., linear motion along the X, Y, Z Cartesian axes) and in three degrees of rotational motion (e.g., rotation about the X, Y, Z Cartesian axes). Additionally, the motors can be used to actuate an articulable end effector of the instrument for grasping tissue in the jaws of a biopsy device or the like.

The teleoperational medical system 100 also includes an image capture system 108 with one or more sub-systems for capturing images from the surgical workspace at the distal end of the medical instrument system 104. The system operator sees images, captured by an image capture system 108, presented for viewing on a display system 110 operatively coupled to or incorporated into the operator input system 106. The display system 110 displays an image or representation of the surgical site and medical instrument system(s) 104 as generated by sub-systems of the image capture system 108. The display system 110 and the operator input system 106 may be oriented so the operator can control the medical instrument system 104 and the operator input system 106 with the perception of telepresence. The display system 110 may include multiple displays such as separate right and left displays for presenting separate images to each eye of the operator, thus allowing the operator to view stereo images.

The teleoperational medical system 100 also includes a fluid management system 109 for delivering or evacuating fluid through the medical instrument system 104. For example, the fluid management system 109 may include a fluid delivery system for delivering air, carbon dioxide, or saline through the instrument to clean the distal end of the instrument. The fluid management system may also include a suction system to remove fluid and debris from the patient internal surgical workspace.

Alternatively or additionally, display system 110 may present images of the surgical site recorded and/or imaged preoperatively or intra-operatively using imaging technology such as computerized tomography (CT), magnetic resonance imaging (MRI), fluoroscopy, thermography, ultrasound, optical coherence tomography (OCT), thermal imaging, impedance imaging, laser imaging, nanotube X-ray imaging, and the like. The presented preoperative or intra-operative images may include two-dimensional, three-dimensional, or four-dimensional (including e.g., time based or velocity based information) images and associated image data sets for reproducing the images.

The teleoperational medical system 100 also includes a control system 112. The control system 112 includes at least one memory and at least one processor (not shown), and typically a plurality of processors, for effecting control between the medical instrument system 104, the operator input system 106, the image capture system 108, and the display system 110. The control system 112 also includes programmed instructions (e.g., a computer-readable medium storing the instructions) to implement some or all of the methods described in accordance with aspects disclosed herein. While control system 112 is shown as a single block in the simplified schematic of FIG. 1, the system may include two or more data processing circuits with one portion of the processing optionally being performed on or adjacent the teleoperational assembly 102, another portion of the processing being performed at the operator input system 106, and the like. Any of a wide variety of centralized or distributed data processing architectures may be employed. Similarly, the programmed instructions may be implemented as a number of separate programs or subroutines, or they may be integrated into a number of other aspects of the teleoperational systems described herein. In one embodiment, control system 112 supports wireless communication protocols such as Bluetooth, IrDA, HomeRF, IEEE 802.11, DECT, and Wireless Telemetry.

In some embodiments, control system 112 may include one or more servo controllers that receive force and/or torque feedback from the medical instrument system 104. Responsive to the feedback, the servo controllers transmit signals to the operator input system 106. The servo controller(s) may also transmit signals instructing teleoperational assembly 102 to move the medical instrument system(s) 104 which extend into an internal surgical site within the patient body via openings in the body. Any suitable conventional or specialized servo controller may be used. A servo controller may be separate from, or integrated with, teleoperational assembly 102. In some embodiments, the servo controller and teleoperational assembly are provided as part of a teleoperational arm cart positioned adjacent to the patient's body.

The teleoperational medical system 100 may further include optional operation and support systems (not shown) such as illumination systems, steering control systems, irrigation systems, and/or suction systems. In alternative embodiments, the teleoperational system may include more than one teleoperational assembly and/or more than one operator input system. The exact number of manipulator assemblies will depend on the surgical procedure and the space constraints within the operating room, among other factors. The operator input systems may be collocated or they may be positioned in separate locations. Multiple operator input systems allow more than one operator to control one or more manipulator assemblies in various combinations.

Figure 2:
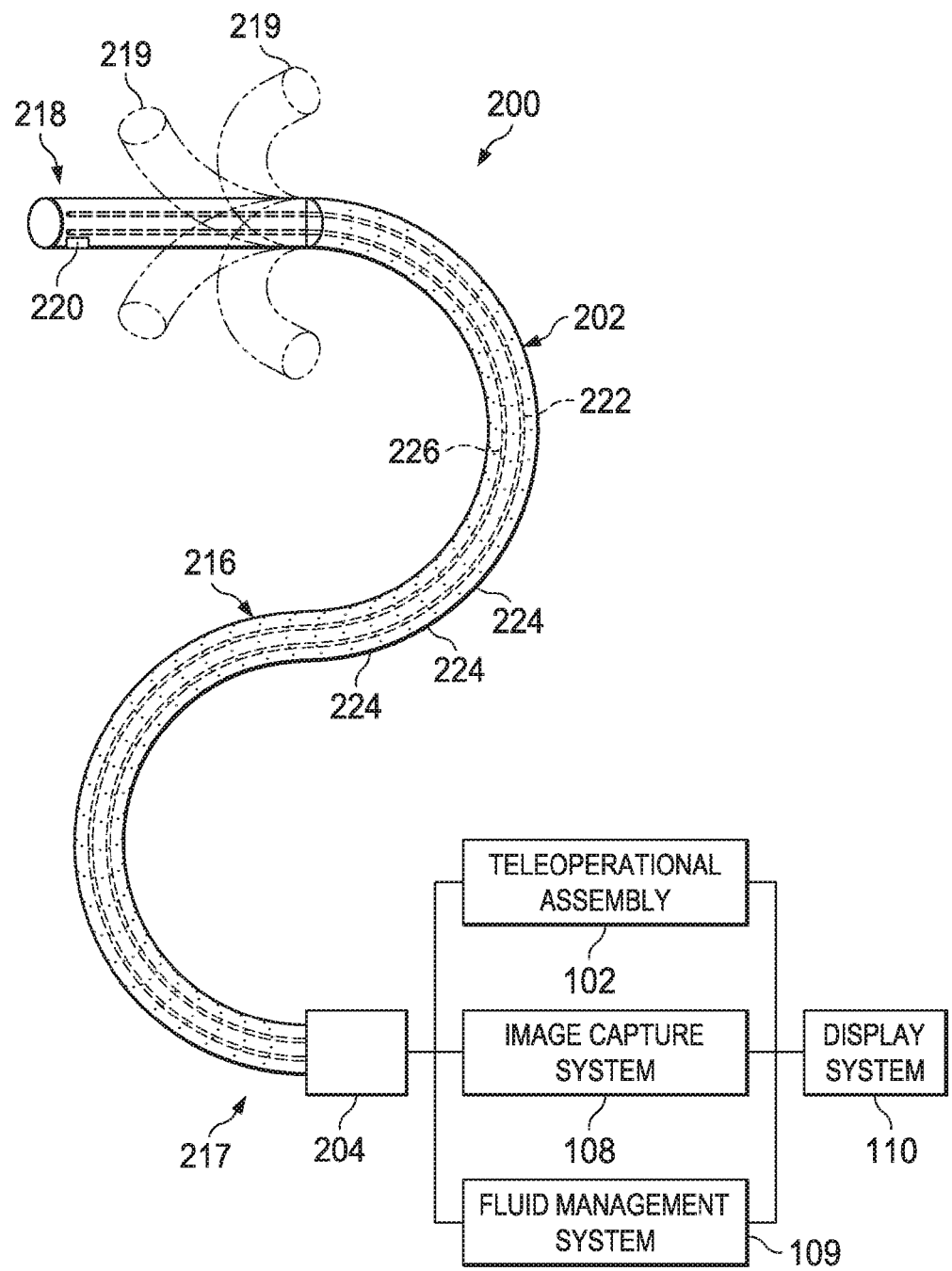
FIG. 2 is a diagram showing an illustrative medical instrument system comprising an endoscopic visualization system, according to one example of principles described herein.

FIG. 2 illustrates a medical instrument system 200, which may be used as the medical instrument system 104 of teleoperational medical system 100 for insertion into a patient's body at either a natural orifice or a surgically created orifice. Alternatively, the medical instrument system 200 may be used for non-teleoperational exploratory procedures or in procedures involving traditional manually operated medical instruments, such as endoscopy.

The instrument system 200 includes a catheter system 202 coupled to an instrument body 204. The catheter system 202 includes an elongated flexible catheter body 216 having a proximal end 217 and a distal end or tip portion 218. In one embodiment, the flexible body 216 has an approximately 3 mm outer diameter. Other flexible body outer diameters may be larger or smaller. The entire length of the body 216, between the distal end 218 and the proximal end 217, may be effectively divided into the segments 224.

The catheter system 202 may optionally include a shape sensor 222 for determining the position, orientation, speed, velocity, pose, and/or shape of the catheter tip at distal end 218 and/or of one or more segments 224 along the body 216. The shape sensor 222 may include an optical fiber aligned with the flexible catheter body 216 (e.g., provided within an interior channel (not shown) or mounted externally). In one embodiment, the optical fiber has a diameter of approximately 200 µm. In other embodiments, the dimensions may be larger or smaller. The optical fiber of the shape sensor system 222 forms a fiber optic bend sensor for determining the shape of the catheter system 202.

The medical instrument system may optionally include a position sensor system 220. The position sensor system 220 may be a component of an EM sensor system with the sensor 220 including one or more conductive coils that may be subjected to an externally generated electromagnetic field.

The flexible catheter body 216 includes one or more working channels sized and shaped to receive an auxiliary instrument 226. Auxiliary instruments may include, for example, image capture probes, biopsy instruments, laser ablation fibers, or other surgical, diagnostic, or therapeutic tools. Auxiliary tools may include end effectors having a single working member such as a scalpel, a blunt blade, an optical fiber, or an electrode. Other end effectors may include, for example, forceps, graspers, scissors, or clip appliers. Examples of electrically activated end effectors include electrosurgical electrodes, transducers, sensors, and the like. In various embodiments, the auxiliary tool 226 may be an image capture probe, such as an endoscope, that includes a distal portion with a stereoscopic or monoscopic camera at or near the distal end 218 of the flexible catheter body 216 for capturing images (including video images) that are processed by the image capture system 108 for display. The image capture probe may include a cable coupled to the camera for transmitting the captured image data. Alternatively, the image capture instrument may be a fiber-optic bundle, such as a fiberscope, that couples to the visualization system. The image capture instrument may be single or multi-spectral, for example capturing image data in one or more of the visible, infrared, or ultraviolet spectrums.

The auxiliary instrument 226 may house cables, linkages, or other actuation controls (not shown) that extend between the proximal and distal ends of the instrument to controllably bend the distal end of the instrument. Steerable instruments are described in detail in U.S. Pat. No. 7,316,681 (filed on Oct. 4, 2005) (disclosing "Articulated Surgical Instrument for Performing Minimally Invasive Surgery with Enhanced Dexterity and Sensitivity") and U.S. patent application Ser. No. 12/286,644 (filed Sep. 30, 2008) (disclosing "Passive Preload and Capstan Drive for Surgical Instruments"), which are incorporated by reference herein in their entireties.

The flexible catheter body 216 may also houses cables, linkages, or other steering controls (not shown) that extend between the housing 204 and the distal end 218 to controllably bend the distal end 218 as shown, for example, by the broken dashed line depictions 219 of the distal end. Steerable catheters are described in detail in U.S. patent application Ser. No. 13/274,208 (filed Oct. 14, 2011) (disclosing "Catheter with Removable Vision Probe"), which is incorporated by reference herein in its entirety. In embodiments in which the instrument system 200 is actuated by a teleoperational assembly, the housing 204 may include drive inputs that removably couple to and receive power from motorized drive elements of the teleoperational assembly. In embodiments in which the instrument system 200 is manually operated, the housing 204 may include gripping features, manual actuators, or other components for manually controlling the motion of the instrument system. The catheter system may be steerable or, alternatively, the system may be non-steerable with no integrated mechanism for operator control of the instrument bending. Also or alternatively, one or more lumens, through which medical instruments can be deployed and used at a target surgical location, are defined in the walls of the flexible body 216.

In various embodiments, the medical instrument system 200 may include a flexible bronchial instrument, such as a bronchoscope or bronchial catheter, for use in examination, diagnosis, biopsy, or treatment of a lung. The system 200 is also suited for navigation and treatment of other tissues, via natural or surgically created connected passageways, in any of a variety of anatomical systems, including the colon, the intestines, the kidneys, the brain, the heart, the circulatory system, and the like. In various embodiments, the medical instrument may include a rigid construction (e.g. a rigid endoscope) rather than a flexible catheter.

Figure 3:
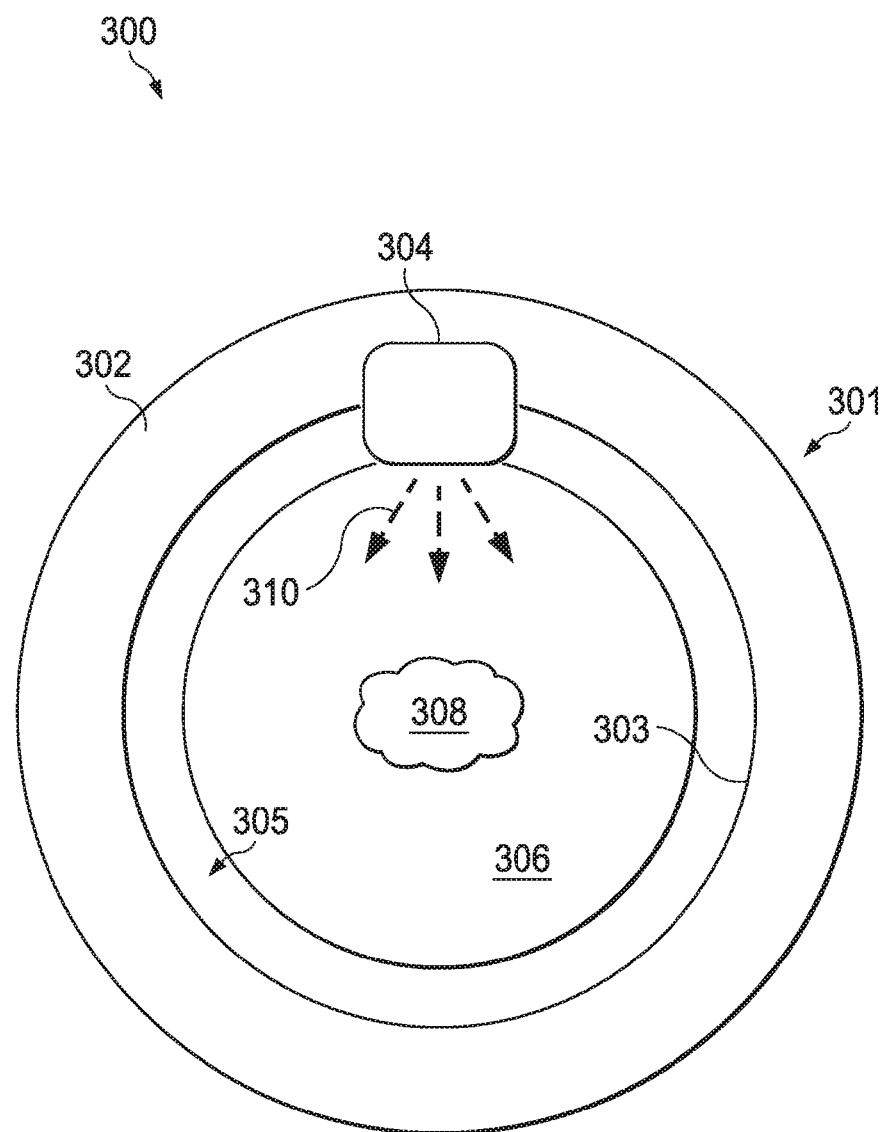
FIG. 3 is a front view of the front of an endoscopic visualization system, according to one example of principles described herein.

In the embodiment of FIG. 2, the instrument 200 is teleoperated within the teleoperational medical system 100. In an alternative embodiment, the teleoperational assembly 102 may be replaced by direct operator control. In the direct operation alternative, various handles and operator interfaces may be included for hand-held operation of the instrument. FIG. 3 is a front view of the front of an endoscopic visualization system, according to one example of principles described herein.

To operate properly, the distal end of instrument 200 or other catheter instruments, bronchoscopes, or endoscopes should remain free of obstructions. The accumulation of patient fluids (e.g., mucous or blood), tissue, or cautery smoke on the lens of the imaging system or at the opening of a catheter working channel may create an obstacle to the safe and time efficient conduct of procedures using such instruments. Some cleaning methods involve injecting a fluid (e.g., gas or saline) through a nozzle aimed at the lens or removing the instrument from the patient and wiping the distal end free of contaminants. Both of these procedures cost time which can affect both patient safety and cost effectiveness. The use of an injected fluid to clean the distal end of the instrument may raise concerns in certain situations; e.g., when the instrument is inserted into a patient lumen (e.g., an airway passage of the lungs) and the outside diameter of the instrument tip completely or substantially fills the inside diameter of the patient lumen, sealing off the anatomical region distal of the instrument tip. Excessive fluid injected to clean the instrument tip may cause the sealed off portion of the anatomical region to overinflate and rupture the surrounding tissue. For example, if the instrument is a bronchoscope in use in a lung, such excess fluid injection into the region of the lung isolated by the impacted instrument may cause a rupturing of the lung wall or pleura, resulting in pneumothorax. According to methods and systems described herein, a more effective cleaning method for an instrument distal end minimizes the fluid discharged into the patient anatomy while adequately removing the obstructing material.

FIG. 3 is a front view 300 of an elongated medical instrument 301, such as an endoscope, a bronchoscope, flexible catheter instrument 200, or rigid imaging instrument. According to the present example, the medical instrument 301 includes catheter 302 with a channel 303 through which an elongated imaging instrument 305 extends. The imaging instrument 305 includes a lens 306. The lens 306 may have an obstruction 308 thereon. The obstruction 308 may include a cloudy substance or an object that obstructs vision through the visualization system. For example, patient tissue or patient fluids, such as blood or mucus, may stick to the surface of the lens 306 and cloud the surface of the lens 306. The obstruction 308 on the lens 306 is visible in images received by the imaging instrument 305 and sent to the user. A nozzle 304 is configured to spray a fluid 310 across the surface of the lens to clear the lens of the obstruction 308. The fluid may be, for example, saline, carbon dioxide, or air. Note that nozzle 304 can be any structure for guiding fluid 310 to a desired output location/configuration.

Figure 4:
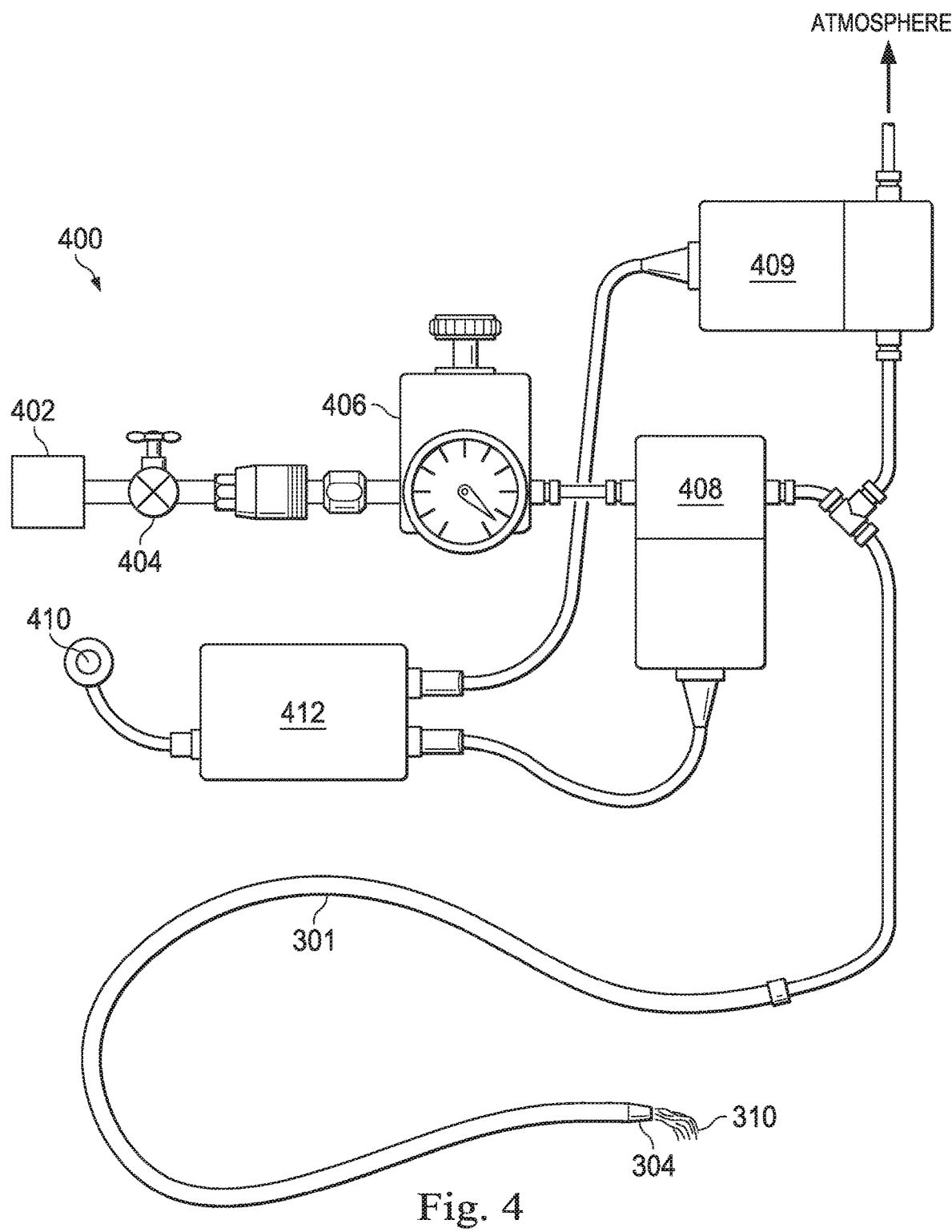
FIG. 4 is a diagram showing an illustrative system to provide pressurized fluid to the lens of an endoscopic visualization system, according to one example of principles described herein.

FIG. 4 is a diagram showing an illustrative fluid delivery system 400 which may be a component of the fluid management system 109. The fluid delivery system 400 provides short bursts of high-pressure fluid 310 from nozzle 304 to the lens 306 of the medical instrument 301 to deliver a low volume of the fluid 310 into the patient anatomy. According to the present example, the system 400 includes a pressurized fluid supply 402, a shutoff valve 404, a pressure regulator 406, a high-speed valve 408, an optional timer 412 controlled by a trigger 410, a fluid supply lumen extending through the medical instrument 301, and the nozzle 304. Together the timer 412 and the trigger 410 may be considered to be a valve control mechanism.

The fluid supply 402 may be pressurized through standard means (e.g., compressed within a chamber) and may be part of an existing pressurized fluid delivery system in the standard suite of utilities available in a surgical environment. The fluid supply 402 may be connected to the system 400 through the shutoff valve 404 that controls the flow of the fluid 310. To monitor and maintain the pressurization of the fluid 310, a pressure regulator 406 may be used.

In some embodiments, the pressure of the fluid 310 may be regulated to be discharged at a pressure of between approximately 50 and 300 psi. In some examples, the pressure of the fluid may be greater than 50, 60, 75, 100, 150 or even 300 psi. The pressure of the fluid supply 402 is greater than a standard pressure supplied by an operating room wall. The standard pressure supply of pressurized fluid in an operating room is approximately 50 psi. In some examples, a pressure augmenting mechanism is used to create the higher pressurized fluid supply 402. Such pressure augmenting mechanisms may include a fluid compressor such as an air compressor. In some examples, the pressure augmenting mechanism may be a pressure amplifier (such as a Model HAA31-2.5 or 85291 manufactured by Haskel). In some examples, the pressure augmenting mechanism may be a high pressure bottled gas that is used in accordance with an appropriate regulator.

In some embodiments, the high-speed valve 408 may be a valve 408 capable of being opened for shorts periods of time (e.g. 0.5 milliseconds) as controlled by the trigger 410 and the timer 412. When the valve 408 is opened, the pressurized fluid 310 is allowed to flow into the fluid supply lumen extending within the medical instrument 301 to the nozzle 304. In one example, the high speed valve 408 is a solenoid valve. In one example, the high speed valve 408 is a Model MHJ-10 series valve manufactured by Festo. Such a valve is capable of handling pressurized fluid with a pressure ranging between 90-130 psi. In one example, the high speed valve 408 is a pneumatic valve.

The valve can be configured to automatically deactivate the flow of pressurized fluid after a predetermined time interval that may be determined by the timer. In some embodiments, the predetermined time interval can be such that the total amount of fluid expended is below a threshold level. The threshold level can be set to reduce the risk of over-inflation of a patient anatomy. The threshold level can take into account the location of the instrument within a patient anatomy. In smaller cavities of the anatomy, it may be desirable to minimize the total amount of fluid expended, and thus the threshold level may be relatively low, such as 0.4 cubic centimeters (ccs). In some slightly larger cavities, a greater threshold level, such as 2 ccs may be used. Larger cavities may have an even larger threshold. In some embodiments, the threshold level can be adjusted according to the location of the instrument, either manually (e.g., by the user based on manipulation of the instrument or viewing of x-ray or imaging data) or automatically (e.g., based on the position of the instrument within the patient anatomy determined by surgical navigation technology or position sensors).

The opening of the high speed valve 408 is controlled by the trigger 410. The trigger 410 will cause the valve 408 to open for a predetermined interval to release a pulse of fluid through the fluid supply lumen of the medical instrument 301 to the nozzle 304. The trigger 410 may be implemented as hardware, software, or a combination of the two. For example, the trigger may be a switch incorporated into the operator input system 106 or at another location within the teleoperational medical system 100 and actuatable by the clinician or an assistant via, for example, motion of the clinician's hand or foot, a verbal command, an eye gaze command, or use of user controlled implement such as a mouse. For example, the trigger 410 may be a foot pedal. The trigger may, alternatively, be provided via a touchpad, finger button, mouse button, or touchscreen button at the operator input system 106. The opening command conveyed via the trigger 410 may be communicated to the valve 408 via the control system 112. In one example, if a clinician notices that the image on the screen (e.g., display 110, FIG. 1) is clouded due to an obstruction, the clinician may manually press the trigger 410.

Although operation of the trigger 410 may be initiated by the clinician or an assistant in response to the visualization of debris on the lens 306, the operation of the trigger may also or alternatively be initiated based upon the system's detection of an obstruction. For example, an optical sensor located at the distal end of the catheter 302 may detect an obstruction. In another example, the control system 112 may monitor the images received via the lens 306 and detect (e.g. through the Fourier transform-based analysis) matter occluding the lens. Based upon this detection, the control system 112 may initiate operation of the trigger.

In some examples, a more sophisticated process may be used to analyze the image from an imaging system of a medical instrument in order to determine whether the lens is dirty. For example, the medical instrument may be within a region of the anatomy where there is less texture and therefore less sharpness and contrast. Sharpness, contrast, and other parameters of an image will be referred to as the clarity of an image. The function for automatically determining if the lens is dirty can factor in the position of the instrument as well as the observed clarity of the image. If the instrument is within a region of the anatomy where less sharpness and contrast is expected, then a threshold amount of clarity can be raised. Thus, even if the image appears somewhat less clear, this does not necessarily mean that the lens is dirty and an automatic pulse of fluid will not be directed across the lens. But, in areas where higher sharpness and contrast is expected, the clarity threshold may be lowered. Thus, when the image appears less clear, it is more likely that this will trigger an automatic pulse of fluid across the lens.

In some examples, a current image can be compared with a recently obtained image to determine if the lens is clouded and should be cleared. For example, in a region with less contrast, the current image can be compared to a recent image. If the current image is substantially more clouded than the recent image, and the medical instrument has not made a significant change in position, then it can be determined that the lens is dirty, and should be cleared. Thus, a pulse of fluid will automatically be triggered.

In some examples, occlusion of the image may be factored into the determination of whether a pulse should be used. For example, if a particular percentage of the image is occluded, then a pulse can be initiated. In one example, a 20% occlusion may trigger the pulse of fluid.

In some examples, a pulse of fluid may be automatically triggered at a specific time interval. For example, a pulse of fluid may be directed across the surface of the lens every 1, 2, or 5 seconds. Other time intervals are contemplated as well. In this example, the user does not have to be concerned with cleaning the lens. Rather, the cleaning of the lens is done automatically for the user and on average, the image remains clearer than without the interval based pulses of fluid.

The closing of the high-speed valve 408 can be controlled by the timer 412. The timer 412 may be set for a predetermined interval. The timer 412 is initiated when the high-speed valve 408 is opened. The timer is set for the predetermined interval. When the predetermined period of time has elapsed, the timer 412 causes the valve 408 to close. For example, the timer may send a signal to the valve instructing the valve to close. The timer may be incorporated into the control system 112 such that the control system sends signals to the valve. In one example, the predetermined period of time may be selected from within a range of approximately 0.5 and 50 milliseconds. In various other embodiments, the performance characteristics of system 400 can be selected or configured to provide a desired fluid pulse time interval without the need for a dedicated timer.

In some examples, the system 400 includes a shunt valve 409 to direct any leakage from the high speed valve 408 away from the catheter passage 303 leading to the nozzle 304. Thus, if there were to be any leakage in the high speed valve 408, this additional fluid would pass through the shunt valve 409 and be directed somewhere else besides the interior of the patient's anatomy. The shunt valve 409 may also be controlled by the trigger 412. Specifically, when the high speed valve 408 is opened to deliver fluid through channel 303 of catheter 302 to nozzle 304, the shunt valve 409 is switched from directing leakage fluid to a drainage line to the OFF or closed condition blocking loss of pressurized fluid from channel 303. In this mode, the valve command to shunt valve 409 is the opposite of the command to fluid delivery valve 408 although in another embodiment there may be overlap in the ON and OFF state timing of the valves. In some examples, a flow sensor can be used to determine if there is a leak in the high speed valve 408 when the valve should be in an OFF position, indicating that fluid should not be flowing at that time. The shunt valve can then be used to direct any leaking fluid away from the patient's anatomy.

In some examples, the pulse of fluid may be a gas. In some cases, the pulse of fluid may be a liquid such as a saline solution. In some examples, pulses of fluid may alternate between a gas and a liquid. This may be done, for example, by using a valve to alternate between a pressurized gas supply and a pressurized liquid supply. In some examples, the final pulse in a series of alternating pulses may be a pulse of gas.

In one example of a conventional fluid delivery system that does not include components such as the pressure regulator, the high-speed valve, the timer, or the trigger, fluid may be supplied at 10 psi for approximately 0.10 seconds, as controlled by the operator, to deliver approximately 10 cc's of fluid through the nozzle, across the lens, and into the patient anatomy.

In one example using the fluid delivery system 400, fluid may be supplied at a higher pressure for a shorter duration to deliver a smaller volume of fluid. For example, at a pressure of 100 psi for a duration of 0.001 seconds controlled by the timer 412, the amount of fluid discharged is approximately 0.316 cubic centimeters (cc). Compared to the conventional system, the system 400 thus may discharge only 3.2% (a 31× reduction) of the fluid but at 10 times (1000% of) the pressure. The greater pressure provides a greater force for dislodging obstructions from the lens and the distal tip of the catheter. The amount of fluid discharged is lower, thus reducing the risk of overinflating the anatomy of the patient sealed off by the catheter. This reduces the risk of tissue perforation or other injury to the patient. The reduced fluid volume may also reduce the drying effect of a sustained air or carbon dioxide jet that can worsen adhesion of lens contaminants. While the reduced volume of fluid expended is beneficial in smaller areas of the anatomy, the principles described herein may be applied to situations where a medical instrument is within a larger cavity of a patient anatomy.

In general, where the fluid is flowing (e.g. a gas or a liquid), the dynamic pressure can be defined as $DP=(\frac{1}{2}) \rho v^2$.

DP is the dynamic pressure; p is the fluid density; and v is the velocity. Thus, the dynamic pressure is dependent upon the velocity squared. The ability to remove an obstruction from a lens depends on the drag force F that a fluid jet exerts on the obstruction. The drag force may be expressed as $F=C_d \times A \times \frac{1}{2}\rho v^2$, where $C_d$ is a drag coefficient of the obstruction and A is a cross-sectional area of the obstruction normal to the flow. Thus the force on the obstruction depends on the square of the fluid velocity. This means that a longer pulse with less pressure will produce substantially more volume and with less force against obstructions on the surface of the lens. Thus, by increasing the pressure and reducing the pulse width, the lens can be more effectively cleared while using a smaller volume of fluid.

For example, using the equation described above, a 12 fold increase in pressure corresponds to approximately a 3.5 fold increase in velocity. Specifically, using the following equations, $P1=\frac{1}{2}\rho v_1^2$ is increased 12 times to $P2=\frac{1}{2}\rho v_2^2$. This equation reduces to $12 \times v_1^2 = v_2^2$, which further reduces to $v_2=3.5\ v_1$. Thus, the volume flow rate for a fluid being applied across the surface of the lens increases approximately 3.5 fold with a pressure increase of 12 fold. But, a substantial reduction in time expending fluid will result in a substantially smaller volume of fluid being applied. For example, changing the width of the pulse from about 0.1 seconds to 0.001 s will result in a 100 fold drop in volume. Combined with the increased pressure, a higher velocity pulse exerting 12× force on the obstruction and having about only 3.5% of the volume can be achieved.

In some embodiments, a high pressure pulse of fluid may be provided by a specific type of pump. For example, some types of pumps that may be used include, but are not limited to, voice coil motor pumps, piezoelectric actuated pumps, servo motor controlled pumps, and solenoid actuated pumps. Such pumps may be used in place of the high speed valve 408, thus allowing very short fluid pulses. In some cases, instead of using a timer, the pumps are configured to create a pulse with the appropriate width in response to a trigger.

Figure 5A:
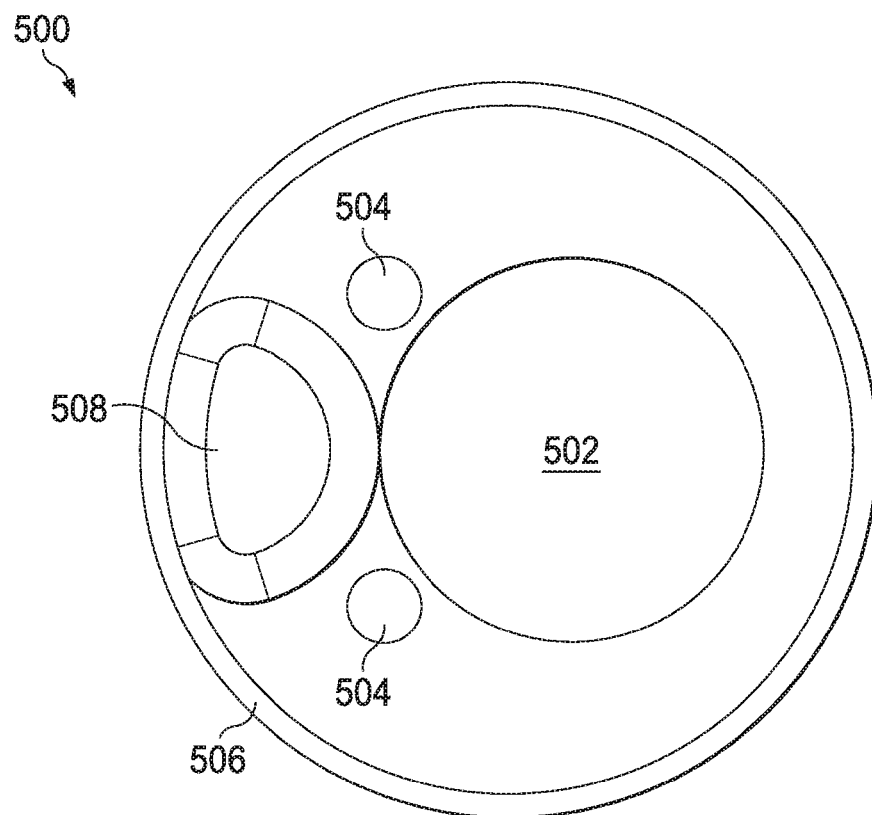
FIG. 5A is a front view of a nozzle for providing fluid to a surface of a lens of an endoscopic visualization system, according to one example of principles described herein.

FIG. 5A is a front view 500 of another embodiment of a medical instrument having a nozzle 508 for providing fluid to a surface of a lens 502. According to this example, the nozzle 508 is positioned adjacent to one side of the lens 502. Illumination fibers 504 are also placed near the lens to light up the interior of the passageways through which the catheter 506 will navigate.

Figure 5B:
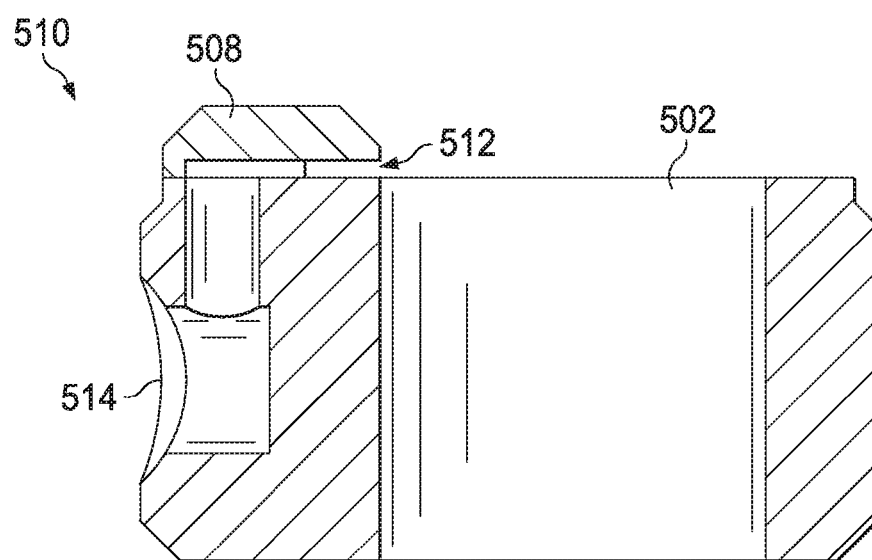
FIG. 5B is a cross-sectional view of a nozzle for providing fluid to a surface of a lens of an endoscopic visualization system, according to one example of principles described herein.

FIG. 5B provides a cross-sectional view of the medical instrument of FIG. 5A. The nozzle 508 is positioned close to the surface of the lens 502. A small opening 512 in the nozzle 508 is positioned and oriented to project fluid parallel and close to the surface of the lens 502. The nozzle 508 may connect to a port 514 that connects to a supply lumen. The fluid delivery system 400 may be used with the nozzle configuration of FIGS. 5A and 5B.

Figure 6:
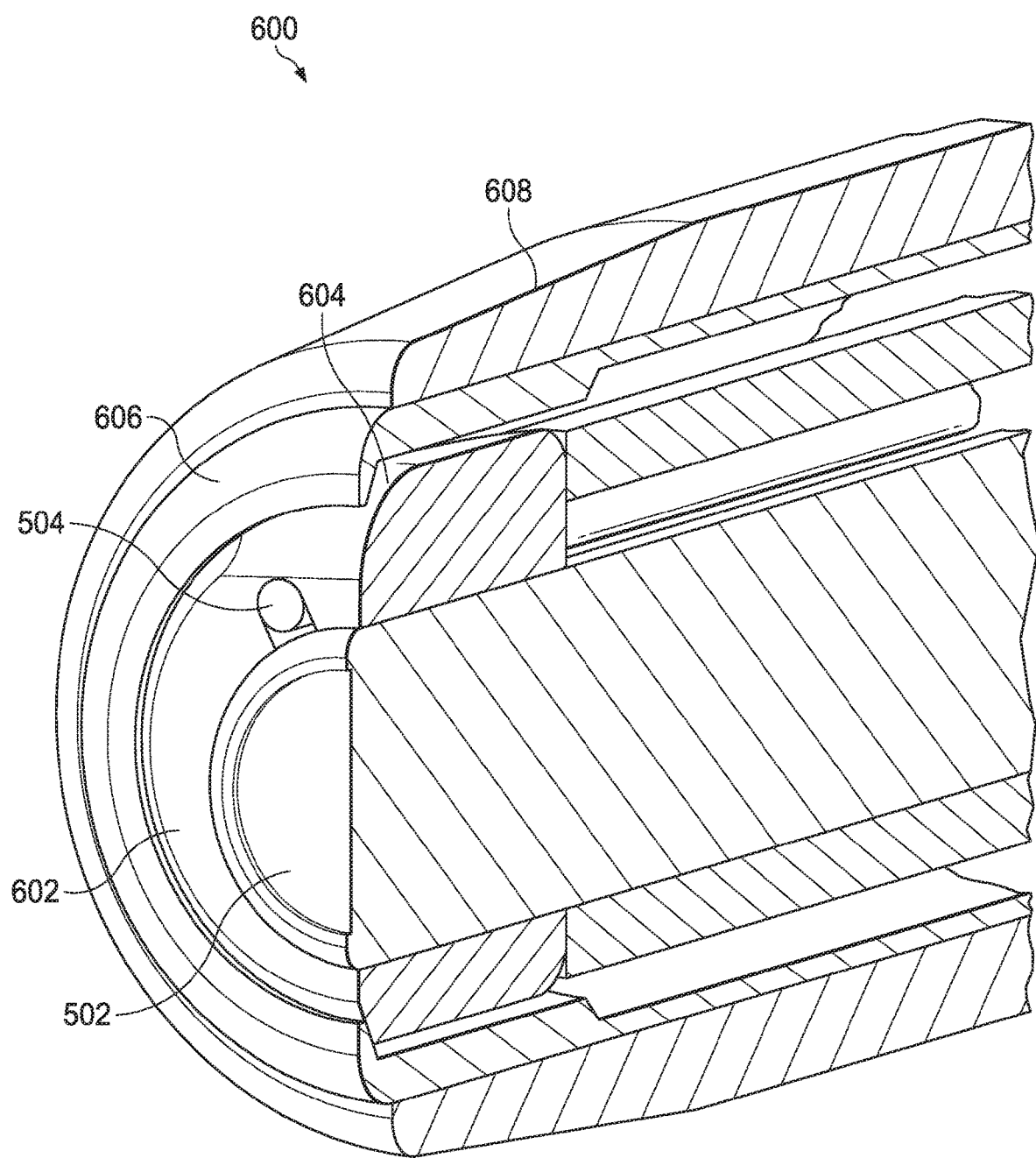
FIG. 6 is a perspective view of a rounded slot nozzle for providing fluid to a surface of a lens of an endoscopic visualization system, according to one example of principles described herein.

FIG. 6 is a perspective view 600 of a rounded or curved slot 604 for providing fluid to a surface of a lens 502 of a medical instrument. According to this example, the nozzle 604 comprises a curved slot 604 between the probe tip 602 and a catheter end piece 604 secured within the catheter jacket 608. With the curved slot 604, the fluid may be delivered through a space between two inner lumens. For example, the fluid may be delivered between the fiber optic cable running through the catheter, and a lumen that circumscribes the fiber optic cable. The fluid may thus be projected from opening 604 at the top of face 602 and centered at 606 across the lens 502 towards the opposite side of the lens exiting at the bottom of face 602. The fluid delivery system 400 may be used with the nozzle configuration of FIG. 6. This medical instrument is described in greater detail in U.S. Patent Application No. [ISRG006000], which is incorporated by reference herein in its entirety.

Figure 7:
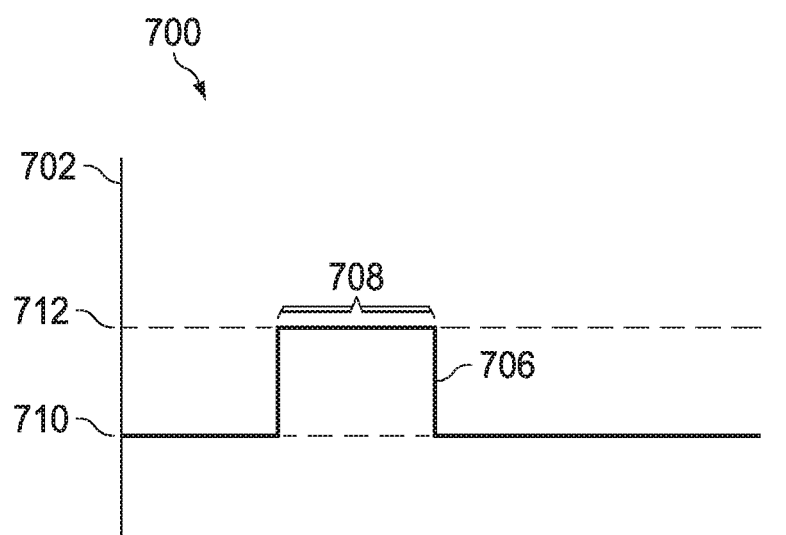
FIG. 7 is a graph showing a pulse signal to cause a pulse of fluid to be applied to a lens of an endoscopic visualization system, according to one example of principles described herein.

FIG. 7 is a graph showing a pulse signal to cause a pulse of fluid to be applied to a lens of a medical instrument. According to the present example, the horizontal axis 704 represents time. The vertical axis 702 represents valve position. Specifically, the valve may be in a closed position 710 or an open position 712. When the valve trigger is initiated, a pulse signal is sent to the valve that opens admitting the pressurized fluid into the supply lumen. The timer is configured to provide a pulse signal 706. The pulse width 708 (i.e., a duration) may be set depending on the desired period of time for applying pressurized fluid to the lens. As described above, the pulse width may range from about 0.5 milliseconds to 50.0 milliseconds. Other ranges for the pulse width are contemplated as well. Generally, the pulse width will be set based on the pressure of the pressurized fluid. As described previously, in some embodiments a higher fluid pressure may permit a disproportionate decrease in pulse duration that provides increased cleaning efficiency while greatly decreasing the volume of fluid delivered.

In some examples, an open loop electric current waveform may be applied to a valve or pump that is used to provide a pulse of fluid. The open loop waveform may be shaped to account for the system dynamics so that the pulse of fluid is applied as desired. For example, the waveform may be shaped such that a pulse has an initial step but then drops slowly. Other types of pulse shapes may be used to cause the fluid pulse to behave as desired. In some cases, however, a closed loop waveform may be used. Thus, a feedback control system can be used to carefully control the opening of a valve or movement of a pump to direct the desired amount of fluid across the surface of the lens. For example, a feedback control loop can be used to control a pump to produce a pulse of fluid that is less than two cubic centimeters.

Figure 8A:
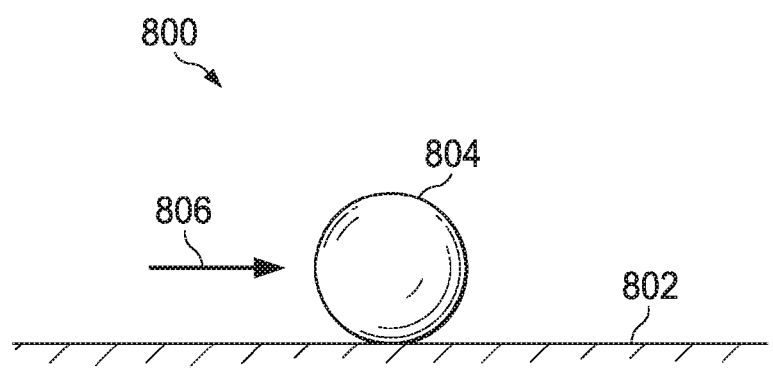
FIGS. 8A and 8B are diagrams illustrating obstructions on the surface of a lens, according to one example of principles described herein.
Figure 8B:
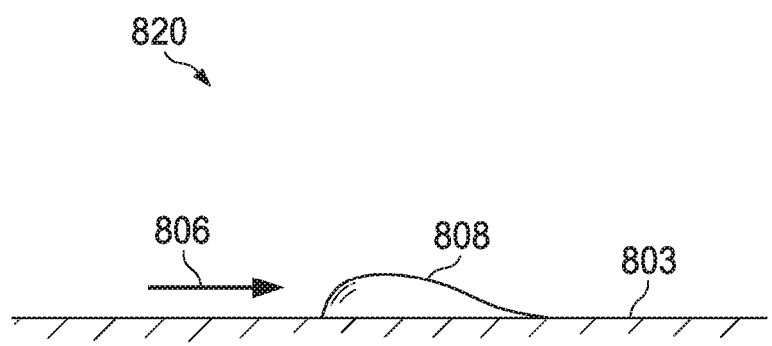

FIGS. 8A and 8B are diagrams illustrating obstructions on the surface of a lens. In some cases, the surface of the lens may be coated with a hydrophobic coating. FIG. 8A illustrates such a case. A hydrophobic coating reduces the degree to which liquid substances adhere to the surface of the lens 802. A liquid substance on the hydrophobic lens surface 802 may be more likely to form round beads 804 as illustrated in FIG. 8A. This creates a higher drag coefficient Cd for the bead of liquid 804 and places the center of the beaded obstruction 804 higher in the flow 806 where the velocity is greater away from the surface of lens 802. This also creates more surface area for the drag force. Specifically, the larger surface area corresponds to A and the higher drag coefficient corresponds to the $C_d$ in the equation described above, $F=C_d \times A \times \frac{1}{2} \rho v^2$ Thus, the force on the liquid droplet is increased due to increases in the drag coefficient, the cross sectional area and the height of the projection into the flow of the fluid pulse applied. Specifically, a pressurized fluid 806 being projected parallel to the surface 802 will catch more of the beaded obstruction 804 and more effectively move or dislodge the obstruction 804. Additionally, the velocity profile of fluid from the nozzle is such that the velocity is reduced at locations closer to the surface to which the liquid droplet is adhered due to the boundary layer, as will be appreciated by one skilled in the art.

FIG. 8B illustrates a hydrophilic surface 803. With a hydrophilic surface, a liquid obstruction 808 adheres firmly and more closely to the surface 803. Thus the drag coefficient and the height of obstruction 808 are reduced. Thus, the portion of pressurized fluid 806 impacting the adhered obstruction 808 will be at a lower velocity and exert a lower force on the more tightly adhered obstruction 808 and will less effectively remove the obstruction. Thus, removing obstructions from the surface of the lens is made more efficient by applying a hydrophobic coating 802 to the surface of the lens. Specifically, a hydrophobic coating has the synergetic beneficial effect of increasing drag forces while reducing adhesion forces when used in conjunction with a jet directed close and parallel to a lens surface and at higher velocities for shorter durations.

Figure 9:
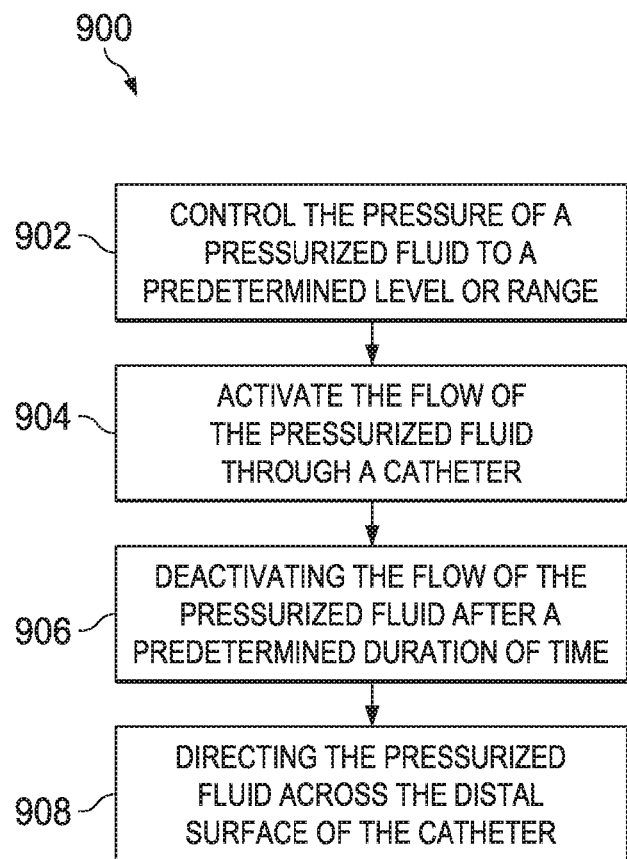
FIG. 9 is a flowchart showing an illustrative method for clearing the lens of an endoscopic visualization system, according to one example of principles described herein.

FIG. 9 is a flowchart showing an illustrative method for clearing the lens of a medical instrument system. According to the present example, the method 900 includes a process 902 for controlling the pressure of a pressurized fluid to a predetermined level or range. A process 904 includes activating the flow of the pressurized fluid through a catheter of the medical instrument. A process 906 includes deactivating the flow of the pressurized fluid after a predetermined duration of time. A process 908 includes directing the pressurized fluid across the distal surface of the catheter. The process may be repeated until the lens of an imaging system in the catheter is cleared of obstruction as determined by a user or by the detection systems described above. In some alternative embodiments, a preset number of pulses may be delivered each time an obstruction is detected or pulses may be delivered at fixed intervals on a continuing basis.

The systems and methods of this disclosure may be used for connected bronchial passageways of the lung. The systems and methods may also be suited for navigation and treatment of other tissues, via natural or surgically created connected passageways, in any of a variety of anatomical systems including the abdomen, colon, the intestines, the kidneys, the brain, the heart, the circulatory system, or the like. The methods and embodiments of this disclosure are also suitable for non-surgical applications.

The systems and methods described herein use the example where the surface being cleared by the high pressure, short pulse of fluid is a surface of a lens of an imaging system. In some cases, however, principles described herein may be applied to other surfaces of instruments that can benefit from cleaning. For example, a pulse of pressurized fluid may be applied to clear the surface of a light delivery tool, the tissue-contacting surface(s) of a surgical tool (e.g., the jaws of a grasper or vessel sealer, the blade of a scalpel, or the sampling structure of a biopsy tool).

One or more elements in embodiments of the invention may be implemented in software to execute on a processor of a computer system such as control processing system 600. When implemented in software, the elements of the embodiments of the invention are essentially the code segments to perform the necessary tasks. The program or code segments can be stored in a processor readable storage medium or device that may have been downloaded by way of a computer data signal embodied in a carrier wave over a transmission medium or a communication link. The processor readable storage device may include any medium that can store information including an optical medium, semiconductor medium, and magnetic medium. Processor readable storage device examples include an electronic circuit; a semiconductor device, a semiconductor memory device, a read only memory (ROM), a flash memory, an erasable programmable read only memory (EPROM); a floppy diskette, a CD-ROM, an optical disk, a hard disk, or other storage device, The code segments may be downloaded via computer networks such as the Internet, Intranet, etc.

Note that the processes and displays presented may not inherently be related to any particular computer or other apparatus. Various general-purpose systems may be used with programs in accordance with the teachings herein, or it may prove convenient to construct a more specialized apparatus to perform the operations described. The required structure for a variety of these systems will appear as elements in the claims. In addition, the embodiments of the invention are not described with reference to any particular programming language. It will be appreciated that a variety of programming languages may be used to implement the teachings of the invention as described herein.

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art.

What is claimed is:

1. A system comprising:
    a nozzle;
    a pressure augmenting mechanism connected to the nozzle, wherein the pressure augmenting mechanism is configured to provide a pressurized fluid at a pressure that is higher than a standard operating room pressure;
    a valve between the pressure augmenting mechanism and the nozzle, the valve configured to control provision of the pressurized fluid from the pressure augmenting mechanism;
    a valve control mechanism; and
    a control system configured to instruct the valve control mechanism to open the valve to release a flow of the pressurized fluid from the pressure augmenting mechanism through the nozzle and over a surface of a medical instrument, wherein an amount of the flow of the pressurized fluid is determined based on a position of the medical instrument in a patient anatomy.

2. The system of claim 1 wherein the valve includes a high-speed valve.

3. The system of claim 2 wherein the high-speed valve comprises a solenoid valve or a pneumatic valve.

4. The system of claim 1 wherein the valve control mechanism includes a trigger comprising at least one of a foot pedal, a finger button, a mouse button, or a touchscreen button.

5. The system of claim 1 wherein the flow of the pressurized fluid is configured to be released for a predetermined duration within a range of about 0.5 to 50 milliseconds.

6. The system of claim 1 wherein the pressure augmenting mechanism is configured to provide the pressurized fluid at a pressure higher than 50 psi.

7. The system of claim 1 wherein the valve comprises a high speed valve, and wherein the system further comprises a shunt valve configured to redirect an excess fluid from the high speed valve.

8. The system of claim 1 wherein the medical instrument comprises an imaging instrument.

9. The system of claim 1 wherein the control system is configured to instruct the valve control mechanism to open the valve to release the flow of the pressurized fluid for a predetermined duration, wherein the predetermined duration is set so that the amount of the flow of the pressurized fluid is below a threshold amount.

10. The system of claim 9 wherein the control system determines the threshold amount based on the position of the medical instrument in the patient anatomy.

11. The system of claim 1 further comprising a shape sensor, wherein the control system is further configured to determine the position of the medical instrument in the patient anatomy based on shape data received from the shape sensor.

12. The system of claim 1 wherein the amount of the flow of the pressurized fluid includes a first amount when the medical instrument is in a first position in the patient anatomy and a second amount when the medical instrument is in a second position in the patient anatomy.

13. The system of claim 12 wherein when the medical instrument is in the first position, the medical instrument is in a first anatomical passageway of the patient anatomy, wherein when the medical instrument is in the second position, the medical instrument is in a second anatomical passageway of the patient anatomy, and wherein the first anatomical passageway is larger than the second anatomical passageway.

14. The system of claim 13 wherein the first amount of the flow of the pressurized fluid is greater than the second amount of the flow of the pressurized fluid.

15. The system of claim 1 wherein the control system is configured to instruct the valve control mechanism to open the valve to release the flow of the pressurized fluid for a predetermined duration.

16. The system of claim 15 wherein the predetermined duration of the flow of the pressurized fluid is based on the position of the medical instrument in the patient anatomy.

17. The system of claim 15 wherein the valve control mechanism includes a timer configured to control the flow of the pressurized fluid for the predetermined duration.

18. The system of claim 1 wherein the valve control mechanism includes a trigger and a timer.

19. The system of claim 18 wherein the trigger comprises at least one of a foot pedal, a finger button, a mouse button, or a touchscreen button, and wherein the timer is configured to control the flow of the pressurized fluid for a predetermined duration.

20. The system of claim 1 wherein the pressure augmenting mechanism comprises a compressor configured to pressurize a fluid to generate the pressurized fluid.

* * * * *